United States Patent
Salsano et al.

(10) Patent No.: US 12,420,003 B2
(45) Date of Patent: Sep. 23, 2025

(54) ENDOVASCULAR DEVICE FOR DYSFUNCTIONAL FISTULAS

(71) Applicants: Antonio Salsano, Chieti (IT); Giancarlo Salsano, Chieti (IT)

(72) Inventors: Antonio Salsano, Chieti (IT); Giancarlo Salsano, Chieti (IT)

( * ) Notice: Subject to any disclaimer, the term of this patent is extended or adjusted under 35 U.S.C. 154(b) by 0 days.

(21) Appl. No.: 17/422,472

(22) PCT Filed: Jan. 22, 2020

(86) PCT No.: PCT/IB2020/050496
§ 371 (c)(1),
(2) Date: Jul. 13, 2021

(87) PCT Pub. No.: WO2020/152600
PCT Pub. Date: Jul. 30, 2020

(65) Prior Publication Data
US 2022/0088283 A1 Mar. 24, 2022

(30) Foreign Application Priority Data
Jan. 23, 2019 (IT) .......................... 102019000000981

(51) Int. Cl.
*A61M 1/36* (2006.01)

(52) U.S. Cl.
CPC ................................ *A61M 1/3655* (2013.01)

(58) Field of Classification Search
CPC .... A61M 1/3655; A61F 2/07; A61F 2/82; A61F 2/848; A61F 2/86; A61F 2/0077
See application file for complete search history.

(56) References Cited

U.S. PATENT DOCUMENTS

| 10,596,017 | B2* | 3/2020 | Hong ...................... A61F 2/07 |
| 11,213,612 | B2* | 1/2022 | Catto ...................... A61L 33/18 |
| 11,229,512 | B2* | 1/2022 | Cully ...................... A61F 2/958 |
| 2013/0274648 | A1* | 10/2013 | Weinberger ......... A61M 1/3655 604/9 |
| 2014/0052231 | A1* | 2/2014 | Lee ..................... A61M 1/3655 623/1.11 |

(Continued)

FOREIGN PATENT DOCUMENTS

CA 2918936 A1 1/2015

*Primary Examiner* — Guy K Townsend
*Assistant Examiner* — Peter Daniel Smith
(74) *Attorney, Agent, or Firm* — Jose Cherson Weissbrot

(57) ABSTRACT

The endovascular device (1) according to the invention comprises a first tubular sheath in turn comprising a fibrous layer (5) made of a fibrous material containing a coherent assembly of fibers. The ends of the device (1) form two expansion sections (7A, 7B) each of which in turn comprises an expander device (70) arranged to radially expand the endovascular device (1) at least in correspondence with the respective expansion section (7A, 7B). The fibrous layer (5), in particular in correspondence with the intermediate section (11) is, on the other hand, prickable and capable of quickly closing and resealing the holes produced by the needles for dialysis, transfusions or injections. This feature allows (20) compared to current devices, to treat malfunctioning dialysis fistulas and to avoid the exclusion of a part of the superficial venous circuit potentially usable for the hemodialysis session, so that the device being a maintenance device for fistulas from dialysis.

12 Claims, 3 Drawing Sheets

(56) References Cited

U.S. PATENT DOCUMENTS

| | | | |
|---|---|---|---|
| 2016/0081783 A1* | 3/2016 | Puckett | A61L 31/146 264/465 |
| 2016/0158038 A1* | 6/2016 | Teitelbaum | A61F 2/90 623/1.13 |
| 2018/0325646 A1* | 11/2018 | Burke | A61L 31/14 |
| 2018/0368968 A1* | 12/2018 | Leeson | D01D 5/0038 |
| 2019/0275293 A1* | 9/2019 | Lenihan | G02F 1/1368 |

* cited by examiner

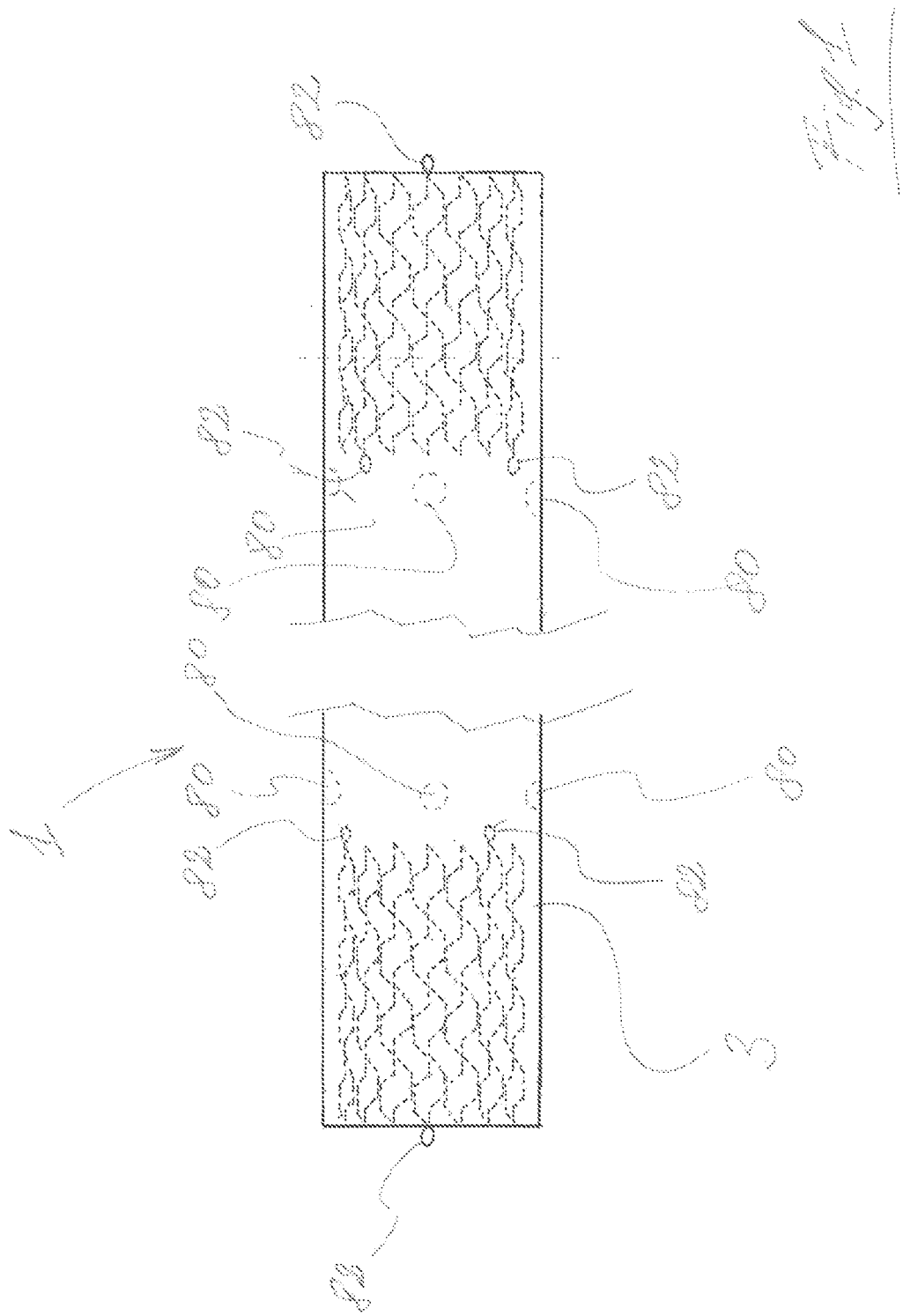

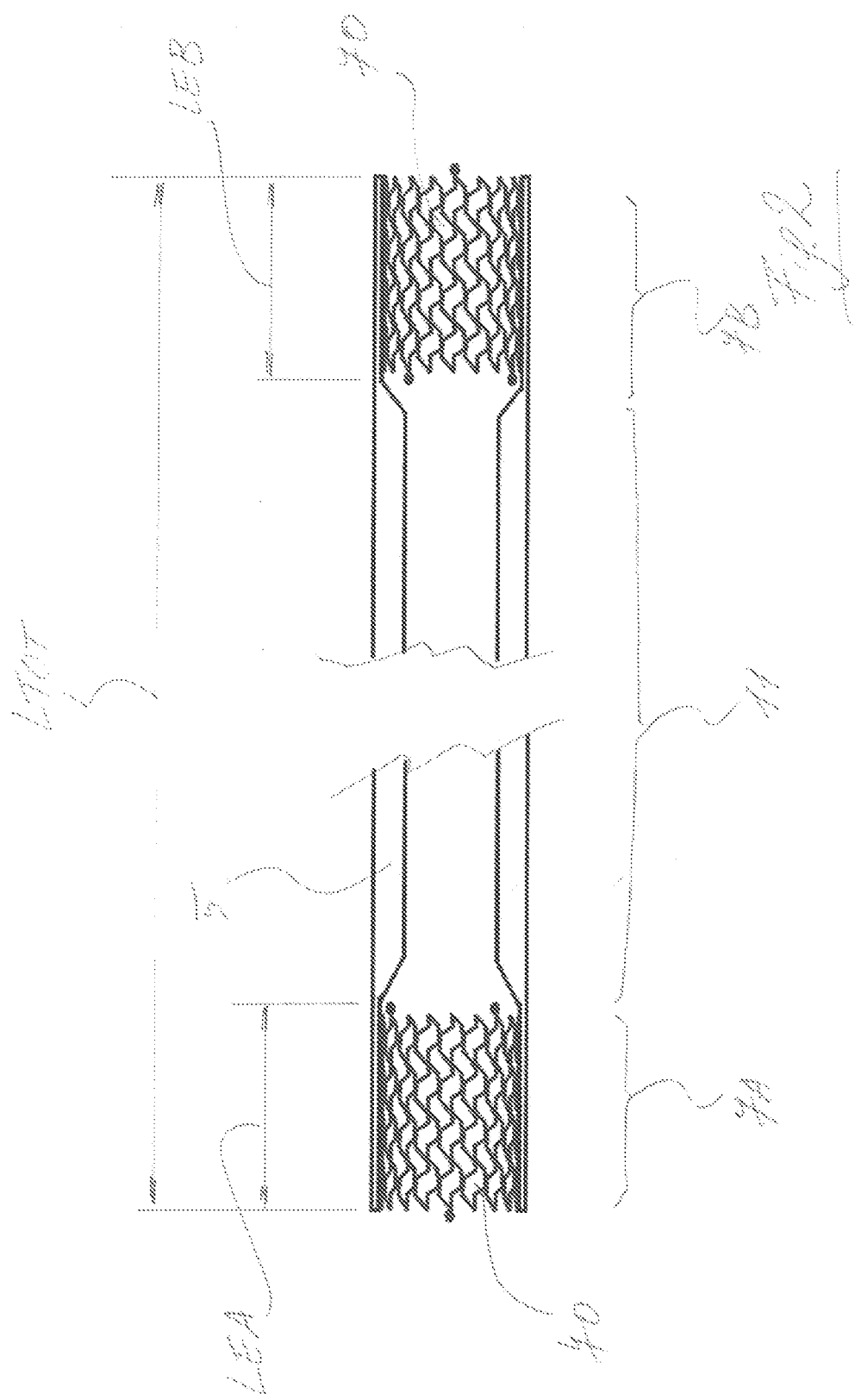

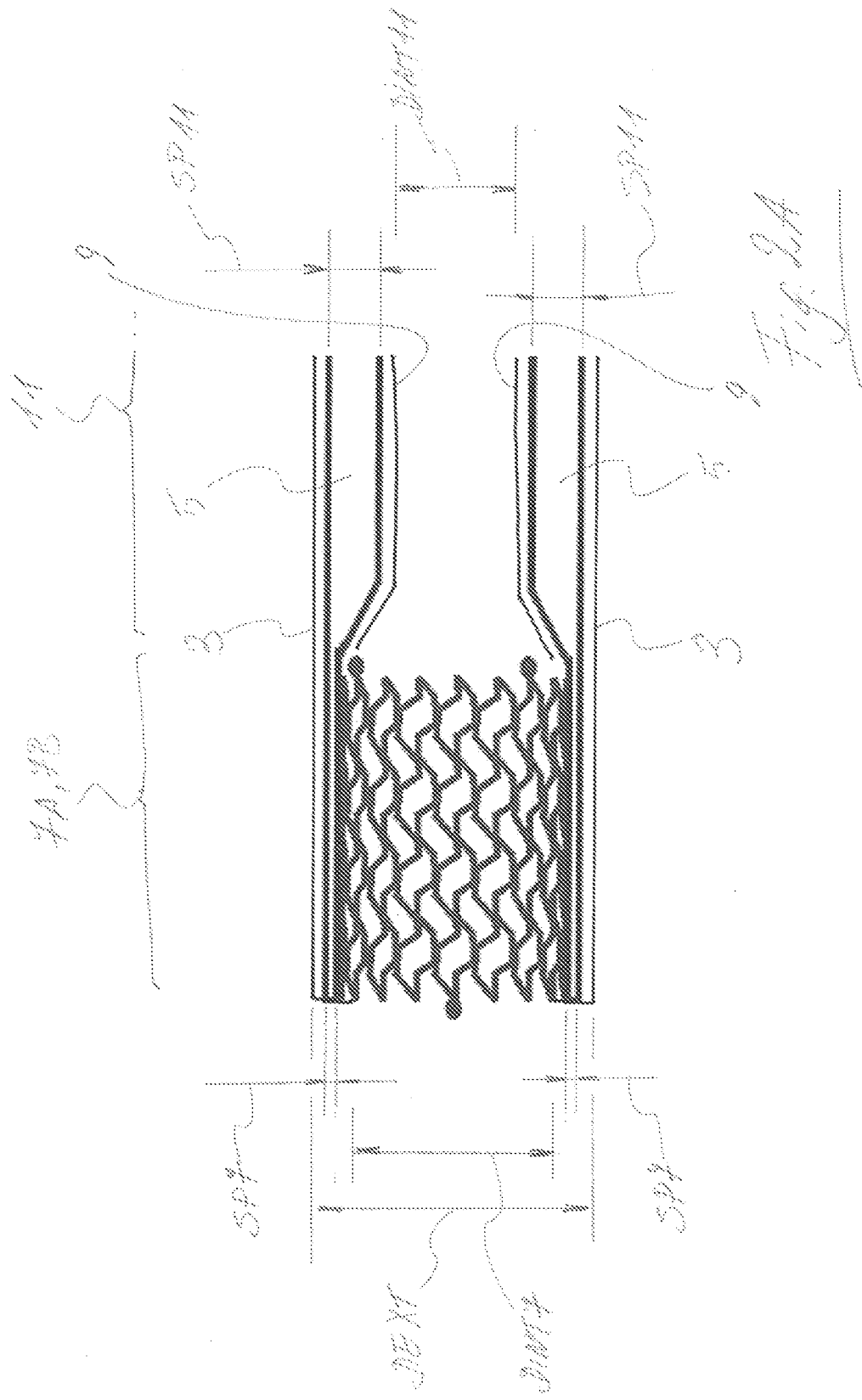

ENDOVASCULAR DEVICE FOR DYSFUNCTIONAL FISTULAS

FIELD OF THE INVENTION

The present invention relates to a new endovascular device particularly indicated for maintaining dialysis fistulas and self-sealing after being punctured, a characteristic which makes it suitable for being punctured repeatedly during hemodialysis sessions.

The invention further relates to a process for producing such an endovascular device.

BACKGROUND

Chronic renal failure affects about 6.3% of the Italian population, specifically, 2.5% of patients are in stage III-IV and need hemodialysis treatment 1 to 3 times in a week.

To perform an effective hemodialysis session, the blood must be able to circulate at a flow between 150 ml/min and 600 ml/min for about 3-4 hours.

The venous flow is inadequate to support these flows while the repeated puncture of the arteries is not advisable due to the high risk of vascular complications.

On those grounds, surgical packaging of an arteriovenous circuit is necessary. Two main types exist: the autogenous fistula (AVF) and the prosthetic fistula (AVG, arteriovenous graft).

An example of a prosthetic fistula is provided in the document US2008/208316, which describes in particular a vascular prosthesis with a tubular structure. The tubular structure comprises at least two layers wherein at least one layer includes a thrombogenic agent. This device is useful for creating a hemodialysis fistula, consisting of a micro and/or nanofiber material with the addition of a thrombogenic coating for the best closure of the hole left by the needle puncture.

This device is a vascular prosthesis implanted surgically, unlike the present invention which intends to describe an exclusively percutaneous installation device suitable to treat malfunctioning pre-existing surgical fistulas such as that described in US'16 (as will be better described below), said device will include two expanders in the terminal parts which serve as anchoring of the device to the AVF/AVG to be treated.

Both types of fistulas performed surgically, as well as the one described in US'16, are subject to various complications following the repeated use of hemodialysis access and limit their duration over time such as stenosis, occlusion and thrombosis of the efferent vessel.

Therefore it is known to prolong the operative life of the fistula through endovascular treatments.

Angioplasty (PTA) still remains the first-line treatment for non-functioning fistulas, but has low long-term patency rates.

The placement of stent grafts after angioplasty is associated with higher rates of primary and secondary patency than angioplasty alone, but their use is limited.

In fact, the stent-grafts currently on the market are not suitable for use in a haemodialysis circuit since they are equipped with expanded polytetrafluoroethylene (ePTFE) sheath and a nitinol skeleton: the puncture of a needle involves a high puncture probability of damaging the nitinol skeleton by breaking or deforming it, and leaves a permanent hole in the ePTFE sheath with the subsequent risk of bleeding, the ePTFE not behaving as a real elastomer.

For these reasons, the positioning of a stent in dysfunctional dialysis fistulas is limited by the exclusion of a part of the superficial venous circuit potentially usable for the haemodialysis session, since current stents cannot be with needles.

An object of the present invention is to overcome the previous drawbacks of the state of the art, providing an endovascular device suitable for applications in the arterial and/or venous blood vessels of a patient on haemodialysis or other body cavities subject to frequent punctures for medical needs, such as haemodialysis treatments.

Therefore, it is an object of the present invention, as mentioned above, to maintain the patency of pre-existing, if dysfunctional, surgical fistulas.

SUMMARY OF THE INVENTION

This scope is achieved, according to a first aspect of the present invention, with an endovascular device having the characteristics according to claim 1.

In an endovascular device according to a particular embodiment of the invention, at least 30% by weight, and preferably 50% by weight, of the fibers of the fibrous layer (5) are formed by long fibers, having an average length equal to or greater than 10 times the average diameter and/or the average width of each fiber.

In an endovascular device according to a particular embodiment of the invention, at least 30% by weight, and preferably 50% by weight, of the fibrous layer is formed by fibers having an average diameter or width equal to or less than 1000 nanometers.

In a particular embodiment of the invention, this endovascular device (1) has an overall length (LTOT) between 5 and 25 centimeters.

In a second aspect of the present invention, this scope is achieved with a process having the characteristics.

Further characteristics of the invention are subject of the dependent claims.

The advantages achievable with the present invention will become clearer to the person skilled in the art from the following detailed description of a particular embodiment of a non-limiting nature, illustrated with reference to the following schematic figures.

BRIEF DESCRIPTION OF THE DRAWINGS

FIG. 1 shows a side view of an endovascular device according to a particular embodiment of the present invention;

FIG. 2 shows a side view, partially in section according to a longitudinal plane, of the endovascular device of FIG. 1;

FIG. 2A shows a detail of the partially sectioned side view of FIG. 2, with one end of the endovascular device of FIG. 1.

DETAILED DESCRIPTION

By resorbable material in the present description is meant a material that can be broken down and reabsorbed by the patient's body where it was implanted.

FIGS. 1, 2, 2A relate to an endovascular device according to a special embodiment of the present invention, indicated with the overall reference 1.

The endovascular device 1 comprises a first tubular sheath preferably formed by a fibrous layer 5 made of a fibrous material containing a coherent assembly of fibers.

In embodiments not shown, the first tubular sheath can more generally comprise a fibrous layer 5 made of a fibrous material containing a coherent assembly of fibers; therefore, in addition to the fibrous material 5, the first tubular sheath 5 can also comprise other elements such as additional layers, sheaths, materials or mechanical, electrical or electronic components.

Advantageously, the endovascular device 1 comprises at least an expansion portion 7A, 7B in turn comprising an expander device 70 arranged to radially expand the endovascular device 1 in correspondence with the respective expansion portion 7A, 7B, making the support rest and adhering the external surface of at least a portion of the device 1 to the internal walls of the blood vessel or other body cavity.

Each expander device 70 can comprise, for example, a substantially tubular mesh, net or cage, per se known, capable of passing from a restricted condition to an expanded condition following a suitable activation command.

Each expander device 70 can have for example the shape of a known stent.

Preferably each expander device 70 is inserted inside the fibrous layer 5.

In a restricted condition, the expander device 70 has radially smaller dimensions while in the expanded condition it has radially larger dimensions.

This substantially tubular mesh, net or cage is preferably made of a shape-resorbable material such as poly (L-lactide) or poly (D, L-lactide) or a suitable shape memory material, such as a suitable wire or nitinol foil or other metal.

Advantageously, at least one expansion portion 7A, 7B is arranged at or near one end of the endovascular device 1.

Advantageously, the endovascular device 1 is provided with at least two expansion portions 7A, 7B each arranged at or near one of the ends of the endovascular device 1 itself.

Advantageously, the endovascular device 1 is provided with a prickly intermediate prosthetic portion 11 which extends between the two ends of the device 1 and is free of expanding devices 70 and other metallic or otherwise rigid bodies free and which if pricked with a needle by injections they would break, tear or perforate permanently.

The expansion portions 7A, 7B and the corresponding expanding devices 70 extend respectively for a length LEA, LEB preferably comprised between 5-15 millimeters, more preferably comprised between 5-10 millimeters.

The endovascular device 1 can have a substantially oblong overall shape.

The endovascular device 1 can have an overall length LTOT for example between 5-25 centimeters, between 5-20 centimeters or between 5-10 centimeters.

A first set of radio-opaque markers 80 they can possibly be inserted in the intermediate portion 11 to facilitate the implantation, under fluoroscopic guidance, of the endovascular prosthesis 1 since the intermediate portion 11, being free of metal mesh, is not visible under X-rays.

Preferably the first markers 80 are incorporated in the fibrous layer 5; alternatively, they can be arranged on its internal and/or external surface.

The first markers 80 can have the shape of, for example, small spheres, discs, strips or plates.

Advantageously, as shown in FIG. 1, the first markers 80 are arranged at the limit between the intermediate portion 11 and the expansion sections 7A, 7B.

In an embodiment not shown, the first markers 80 can be arranged with regular or irregular distribution on other areas of the sides of the device 1.

Preferably, each expanding device 70 comprises one or more second radio-opaque markers 82, which may also have the shape of, for example, discs or small spheres.

The second radio opaque markers 82 can be obtained integrally in one piece from the rest of the relative expander device 70, and if necessary with the latter, be incorporated in the fibrous layer 5.

Advantageously, the fibrous layer 5 extends at least in correspondence with said intermediate portion 11.

Advantageously, the fibrous layer 5 does not extend in correspondence with at least said two expansion portions 7A, 7B.

The fibrous layer 5 also extends in correspondence with the two expansion portions 7A, 7B, and more preferably along the entire length of the endovascular device 1.

The external diameter DEXT of the endovascular device 1 can for example be between 4-13 millimeters or between 5-10 millimeters, and for example equal to about 8 millimeters.

The fibrous layer 5 in the intermediate portion 11 has a thickness SP11 greater than the thickness SP7 which it has in the two expansion portions 7A, 7B, so as to make the intermediate portion 11 able to close the perforations made for example by needles for injections after a greater number of punctures (FIG. 2A) avoiding consistent bleeding.

For this purpose the thickness SP11 is preferably between 0.3-1.3 millimeters, more preferably between 0.5-1 millimeters and even more preferably between 0.5-0.8 millimeters.

Again for this purpose the thickness SP7 is preferably between 0.1-1 millimeters, more preferably between 0.2-0.6 millimeters and even more preferably 0.3-0.5 millimeters.

Again for this purpose, the internal diameter DINT11 of the device at the intermediate portion 11 is preferably between 4.5-9.2 millimeters.

Again for this purpose, the internal diameter DINT7 of the device in correspondence with the expansion portions 7A, 7B is preferably between 4.5-9.5 millimeters.

The internal diameters DINT7, DINT11 are measured with reference to the internal wall of the tubular sheath formed by the fibrous layer 5, if the endovascular device 1 is free of any second internal tubular sheath 9 a described hereinafter more in details, while they internal diameters are measured with reference to the internal wall of any second internal tubular sheath 9 if present.

Preferably the fibrous layer 5 contains an assembly of relatively long fibers with an average length equal to or greater than 10 times the average diameter and/or the average width of each fiber; more preferably the fibers have an average length equal to more than 20 times, and even more preferably equal to or greater than 30 times the average diameter or the maximum width—with reference to the same cross section—average of each fiber, where these average values are calculated by averaging them over the length of the fiber itself.

Such fibers are preferably nanofibers or 15 microfibers, meaning by nanofibers of fibers with a linear density less than 0.3 dtex and by microfibers of fibers with a linear density between 0.3 dtex and 1 dtex.

The diameter or the maximum width of the nanofibers can be for example between 200-1000 nanometers, between 300-900 nanometers or between 450-800 nanometers.

Advantageously, the fibers of the fibrous layer 5 are intertwined together, even randomly, so as to make the layer 5 substantially continuous with a certain coherence and mechanical resistance, for example to traction or tearing.

Preferably the consistency and the tensile strength of the fibrous layer 5 is at least equal to the wadding.

The density, arrangement and interconnection of the fibers can for example be more or less similar to that of the fibers of a felt, even if for example not necessarily so compact.

Optionally, the endovascular device 1 can comprise further tubular sheaths such as a second internal tubular sheath 9 contained in the fibrous layer 5 and/or a third external tubular sheath 3 containing the fibrous layer 5.

As for example in FIG. 2A the second internal tubular sheath 9 can internally coat the fibrous layer 5 or in any case be enclosed by it.

As for example in FIG. 2A the third external tubular sheath 3 can externally coat the fibrous layer 5 or otherwise enclose it.

Each of the further tubular sheaths 3, 9 can be formed for example from a substantially continuous non-fibrous layer and also preferably in the form of a substantially tubular sleeve of expanded polytetrafluoroethylene (ePTFE).

The possible further tubular sheaths 3 and 9 have a thickness preferably between 0.1-0.7 millimeters, and more preferably between 0.2-0.5 millimeters.

The fibrous layer 5 can be advantageously made by means of an electrospinning process. Advantageously, the fibrous layer 5 contains fibers based on one or more of the following materials: a polyurethane resin or other non-absorbable polymeric material, poly (carbonate-urea) urethane.

In this regard, the fibrous layer 5 can contain for example at least 10% by weight of the aforementioned resins and polymeric materials, more preferably at least 30% by weight, more preferably at least 50% by weight and even more preferably at least 70-80% by weight.

An example of possible use and operation of the endovascular device 1 is now described.

In a patient, an autogenous fistula is surgically created which connects an artery with a vein, i.e. creating an arteriovenous circuit. This is identical to what occurs in the US document where a graft or surgical fistula is made.

The endovascular device 1 is inserted inside the dialysis fistula or at the arteriovenous graft, as in US'16, when it begins to shrink or occlude after a certain number of punctures.

When the endovascular device 1 is inserted into the fistula by means of a percutaneous catheter, the expanding devices 70 are restricted and the intermediate section 11 folded back on itself.

The two expansion sections 7A, 7B and the relative expander device 70 are preferably positioned upstream and downstream of the stenosis or other occlusion of the fistula, so as to facilitate the opening of the device.

In particular, the two expansion sections 7A, 7B and the relative expander device 70 are preferably positioned in correspondence with healthy sections of veins or arteries.

The expanding devices 70 are subsequently expanded radially so as to adhere to the internal walls of the fistula preventing the endovascular device 1 from flowing along.

The prickable intermediate section 11, without expanding devices 70, is expanded under the thrust of the bloodstream.

The expansion of the whole device can be facilitated for example by pre-assembling the device 1 on an angioplasty balloon or by means of a pull-back system which allows the radial expansion of the expandable ends 7A, 7B and generates a blood flow in the prosthetic area 11 of the device favoring expansion.

The endovascular device 1, once released and dilated, keeps the fistula dilated and pervious and can be pricked several times at the intermediate section 11 to perform, for example, hemodialysis treatments.

Over time, the fibrous layer 5 is endothelized, that is coated inside by a layer of cells from the internal walls of the blood vessels; this cell layer forms a continuous barrier with the healthy ends of the fistula or other blood vessel to which the device 1 is anchored, generating contiguity of the anchoring sections of the device 1 to the patient's blood vessels and preventing bleeding.

Therefore, by referring to document US'16 the present invention could be useful to restore the patency of the US invention, if it is malfunctioning; whereby the two inventions are not superimposable, but can be integrated, so that they are not equal to each other nor have the same purposes. Furthermore, the US device is made up of clearly visible layers, one of which is made up of thrombogenic material. The present invention contains a central fibrous layer which has been reported for convenience and clarity in the drawings as consisting of different layers. However, the layers are all formed of nanofibers and lead to the production of a single tubular element, such that it cannot be identified as stratified. The layers (as visible in the figures) only serve to identify the different thickness between the central and peripheral area of the fibrous layer of our invention and to make clear that the nanofibers are arranged in different directions in each layer to facilitate the closure of the hole after needle puncture.

The US device, containing thrombogenic material, allows puncture even before the endothelization of the device. Unlike our invention which provides puncture only after about 7-10 days after implantation, following endothelization of the internal layer, as described above. The present invention has, as its purpose a simple installation that does not involve surgery and above all the maintenance of pre-existing fistulas so as not to have to create new ones to the patient's benefit.

The fibrous layer 5, in correspondence with the intermediate section 11, as already described, on the other hand, is prickable and capable of quickly closing and sealing back the holes produced by the needles for dialysis, transfusions or injections.

If it is made of non-resorbable microfibers, the fibrous layer 5 does not disappear over time avoiding wear of the device, which would cause irregular thickness and resistance to punctures, and therefore potentially prone to bleeding, breakage following repeated punctures, and restenosis; the device 1 is therefore more reliable and has a longer operating life.

The expansion sections 7A, 7B keep the blood vessel in which they are inserted thanks, to their expanding devices 70 durably dilated; if made of a material reabsorb able by the organism, in the event a restenosis is formed inside the device 1, the fistula can be made pervious again, so renewed, by positioning a second device 1, for example inside the first, covering the restenosis, thus avoiding losing an area of the prickable dialysis fistula.

The possible second tubular sheath or second tubular sheaths in expanded polytetrafluoroethylene (ePTFE) further improves hemostasis after each puncture.

The previously described endovascular device 1 is particularly advantageous, for example, to remedy all types of lesions that occur in a fistula created surgically or more generally in the blood circuit, such as: thrombosis; complex stenosis, i.e. 50% residual stenosis after PTA (PercutaneousTransluminalAngioplasty), PTA not effective vein grafting after angioplasty; recurring stenosis, i.e. a number of PTA equal to or greater than 3 and within 6 months; and exclusion of pseudo aneurysms.

In fact, repeated punctures can cause a complication known as pseudoaneurysm, that is, the wall of the vessel is damaged and the blood is disposed to create a cavity in the context of the surrounding soft tissues.

Pseudoaneurysm carries a risk of bleeding if this newly formed cavity breaks along with compression problems of surrounding structures such as nerves.

The insertion of an endovascular prosthesis with proximal and distal landing on healthy vein sections prevents the pseudoaneurysm, avoiding the passage of blood from the injured vessel to the newly formed cavity.

The fibrous layer 5, in correspondence with the intermediate section 11, is prickable and capable of quickly closing and sealing back the holes produced by the needles for dialysis, transfusions or injections.

This feature allows, compared to current devices, for the treatment of malfunctioning dialysis fistulas and to avoid the exclusion of a part of the superficial venous circuit potentially usable for the hemodialysis session.

The self-sealing ability and long-term patency of device 1 have the ability to increase the survival of dialysis fistulas to improve the quality and length of a patient's life.

The examples of embodiments previously described are susceptible to various modifications and variations without departing from the scope of protection of the present invention.

For example, each reference in this description to "one embodiment", "one exemplary embodiment" means that a particular feature or structure described in relation to the embodiment is included in at least one embodiment of the invention and in a particular variant of the invention as defined in a main claim.

The fact that these expressions appear several times in the description does not imply that they necessarily refer only to the same embodiment.

Furthermore, when a characteristic, element or structure is described in relation to a particular embodiment, it is observed that it falls within the competence of the average technician to apply this characteristic, element or structure to other embodiments.

Numerical references that differ only in quotes, e.g. 21', 21", 21/// when not otherwise specified indicate different variants of an element called in the same way.

Furthermore, all the details can be replaced with other technically-equivalent elements.

For example, the materials used, as well as the dimensions, may be any according to the technical requirements.

It must be understood that an expression of the type "A includes B, C, D" or "A is formed by B, C, D" also includes and describes the particular case in which "A is consisting of B, C, D".

The expression "A includes a B element" unless otherwise specified is to be understood as "A includes one or more elements of B".

The examples and lists of possible variants of the present application are to be understood as non-exhaustive lists.

What is claimed is:

1. An endovascular device (1) for dysfunctional dialysis surgical fistulas, comprising:
   a first tubular sheath (3);
   a second tubular sheath comprising a fibrous layer (5) made of a fibrous material containing a coherent set of fibers, wherein the second tubular sheath includes two lateral ends, and the second tubular sheath is enclosed in entirety, by the first tubular sheath (3);
   a third tubular sheath (9) enclosed, in entirety, by the second tubular sheath, wherein a thickness of the third tubular sheath (9) is same as a thickness of the first tubular sheath (3),
   at least two expansion sections (7A, 7B), wherein each expansion section (7A, 7B) of the at least two expansion sections (7A, 7B) comprise an expander device (70) arranged to radially expand the endovascular device (1) at least in correspondence with the respective expansion sections (7A, 7B), wherein
      the expander device (70) positioned at each end of the endovascular device (1) is disposed inside the fibrous layer (5),
      the expander device (70) includes a first end and a second end,
      said endovascular device (1) forms two ends and comprises an intermediate section (11) which extends between the two ends of the endovascular device (1) and is devoid of the expander device (70) and others metal bodies, so that the intermediate section (11) closes or tends to repeatedly close holes produced by a needle for haemodialysis treatments, each of the fibrous layer (5), the first tubular sheath (3), and the third tubular sheath (9) extends at least in correspondence with said intermediate section (11), the fibrous layer (5), in correspondence with the intermediate section (11), is prickable and able to close and reseal quickly, and the intermediate section (11) maintains a shape optimal for quick resealing of the holes after puncture, wherein
         the intermediate section includes a tapered portion and a non-tapered portion, the tapered portion includes a periphery, a thickness of the fibrous layer (5) in the non-tapered portion is greater than a thickness of the fibrous (5) in the periphery of the tapered portion, and the thickness of the fibrous layer (5) in the periphery is greater than a thickness of the fibrous layer (5) in each of the expansion section (7A, 7B),
      the first end of the expander device (70) is towards the intermediate section, the second end of the expander device (70) is at both lateral ends of second tubular sheath,
      said fibrous layer (5) endothelized after a time period,
      an internal diameter (DINT11) of the expander device (70) across an entire cross-section, at the intermediate section (11) is smaller than an internal diameter (DINT7) of the expander device (70) at each of the expansion section (7A, 7B), and
      said endovascular device (1) being a device for the treatment of the dysfunctional surgical fistulas, adapted to be inserted inside the dysfunctional surgical fistula, when the endovascular device begins to shrink or occlude after a certain number of punctures, to keep the endovascular device pervious, increasing the survival of the dialysis fistulas;
   a first set of markers (80) between the intermediate section (11) and the at least two expansion sections (7A, 7B), and
   a second set of markers (82) wherein a first marker of the second set of markers (82) is at the first end of the expander device (70) and a second marker of the second set of markers (82) is externally adjacent to the second end of the expander device (70), wherein a shape of the first set of markers (80) is same as a shape of the second set of markers (82).

2. The endovascular device (1) according to claim 1, wherein the two ends and the at least two expansion sections (7A, 7B) are placed at or near a respective end of the endovascular device (1).

3. The endovascular device (1) according to claim 1, wherein the fibrous layer (5) extends substantially widely over an entire length of the endovascular device (1).

4. The endovascular device (1) according to claim 1, wherein at least part of the set of fibres of the fibrous layer (5) are obtained by electrospinning and the fibrous layer (5) comprises fibers based on one or more of the following materials: a polyurethane resin, a polymeric material which preclude to be absorbed by the organism in which the endovascular device (1) is implanted.

5. The endovascular device (1) according to claim 1 wherein the fibrous layer (5) which preclude to disappear with the passage of time, avoiding wear of the endovascular device which would present irregular thickness and resistance to punctures, and therefore would be prone to bleeding, to breakage as result of repeated punctures, and restenosis.

6. The endovascular device (1) according to claim 1, wherein the expander device (70) comprises one or more elements realized in a memory shape material including a metallic material.

7. The endovascular device (1) according to claim 1, wherein the expander device (70) comprises one or more elements made of a shape memory material including an environmentally absorbable polymeric material based on poly (L-lactide) or poly (D, L-lactide), so that in the event a restenosis is formed inside the endovascular device (1), the fistula is renewed by positioning a second endovascular device inside a first endovascular device, to cover the restenosis, and avoid losing an area of the dialysis fistula that is prickable.

8. The endovascular device (1) according to claim 1, wherein the third tubular sheath (9) is made of a material chosen from the following group: polytetrafluoroethylene, expanded polytetrafluoroethylene, a resin optionally expanded synthetic, one or more optionally expanded fluorinated polymers, one or more optionally expanded perfluorocarbons.

9. A method for realizing an endovascular device (1) having
a first tubular sheath (3);
a second tubular sheath comprising a fibrous layer (5) made of a fibrous material containing a coherent set of fibers, wherein the second tubular sheath includes two lateral ends, and the second tubular sheath is enclosed, in entirety, by the first tubular sheath (3);
a third tubular sheath (9) enclosed, in entirety, by the second tubular sheath, wherein a thickness of the third tubular sheath (9) is same as a thickness of the first tubular sheath (3);
at least two expansion sections (7A, 7B) wherein each expansion section (7A, 7B) of the at least two expansion sections (7A, 7B) comprises an expander device (70) arranged to radially expand the endovascular device (1) at least in correspondence with the respective expansion sections (7A, 7B), wherein
the expander device (70) positioned at each end of the endovascular device (1) is disposed inside the fibrous layer (5),
the expander device (70) includes a first end and a second end,
said endovascular device (1) forms two ends and comprises an intermediate section (11) which extends between the two ends of the endovascular device (1) itself and is devoid of the expander device (70) and metal bodies, so that the intermediate section (11) closes or tends to repeatedly close holes produced by a needle for haemodialysis treatments, each of the fibrous layer (5) the first tubular sheath (3), and the third tubular sheath (9) extends at least in correspondence with said intermediate section (11), the fibrous layer (5), in correspondence with the intermediate section (11), is prickable and able to close and reseal quickly and the intermediate section (11) maintains a shape optimal for quick resealing of the holes after puncture, wherein
the intermediate section includes a tapered portion and a non-tapered portion, the tapered portion includes a periphery, a thickness of the fibrous layer (5) in the non-tapered portion is greater than a thickness of the fibrous (5) in the periphery of the tapered portion, and the thickness of the fibrous layer (5) in the periphery is greater than a thickness of the fibrous layer (5) in each of the expansion section (7A, 7B),
the first end of the expander device (70) is towards the intermediate section, the second end of the expander device (70) is at both lateral ends of the second tubular sheath,
said fibrous layer (5) is endothelized after a time period,
an internal diameter (DINT11) of the expander device (70) across an entire cross-section, at the intermediate section (11) is smaller than an internal diameter (DINT7) of the expander device (70) at each of the expansion section (7A, 7B), and
said endovascular device (1) being a device for the treatment of the dysfunctional surgical fistulas, adapted to be inserted inside the dysfunctional surgical fistula, when the endovascular device begins to shrink or occlude after a certain number of punctures, to keep the endovascular device pervious, increasing the survival of the dialysis fistulas;
a first set of markers (80) between the intermediate section (11) and the at least two expansion sections (7A, 7B); and
a second set of markers (82) wherein a first marker of the second set of markers (82) is at the first end of the expander device (70) and a second marker of the second set of markers (82) is externally adjacent to the second end of the expander device (70), wherein a shape of the first set of markers (80) is same as a shape of the second set of markers (82),
the method comprising:
forming at least part of the fibres of the fibrous layer (5) by electrospinning.

10. The endovascular device (1) according to claim 1, wherein the internal diameter (DINT11) of the expander device (70) at the intermediate section (11) is preferably between 4.5-9.2 millimeter.

11. The endovascular device (1) according to claim 1, wherein the internal diameter (DINT7) of the expander device at the expansion section (7A, 7B) is preferably between 4.5-9.5 millimeter.

12. The endovascular device (1) according to claim 1, wherein the internal diameter (DINT11, DINT7) is measured with reference to an internal wall of a second tubular sheath (9).

* * * * *